United States Patent [19]

Roth et al.

[11] Patent Number: 5,698,260

[45] Date of Patent: Dec. 16, 1997

[54] METHOD AND APPARATUS FOR COATING CONTAINERS

[75] Inventors: Jonathan N. Roth, Goshen; Gordon Bontrager, South Bend, both of Ind.

[73] Assignee: RCR Scientific, Inc., Goshen, Ind.

[21] Appl. No.: 491,217

[22] Filed: Jun. 16, 1995

[51] Int. Cl.⁶ .................... B05D 7/22; B05B 13/06
[52] U.S. Cl. .................. 427/235; 427/2.22; 427/294; 427/345; 427/346; 427/384; 427/385.5; 427/553; 118/56; 118/70; 118/306; 118/324; 118/408; 118/641; 118/643
[58] Field of Search .................. 427/2.22, 235, 427/346, 553, 443.2, 294, 384, 385.5, 345; 118/56, 641, 643, 306, 408, 70, 324

[56] References Cited

U.S. PATENT DOCUMENTS

| | | | |
|---|---|---|---|
| 1,602,835 | 10/1926 | Reifsnyder | 427/235 |
| 2,105,906 | 1/1938 | Demers | 427/235 |
| 2,755,205 | 1/1956 | Robb et al. | 427/235 |
| 2,976,176 | 3/1961 | Parks | 427/235 |
| 3,928,136 | 12/1975 | Launey | 195/54 |
| 4,170,861 | 10/1979 | Snyder et al. | 53/468 |
| 4,262,091 | 4/1981 | Cox | 435/253 |
| 4,565,783 | 1/1986 | Hansen et al. | 435/299 |
| 4,656,130 | 4/1987 | Shoshan | 435/30 |
| 4,988,302 | 1/1991 | Smith et al. | 435/298 |
| 5,089,413 | 2/1992 | Nelson et al. | 435/254 |

FOREIGN PATENT DOCUMENTS 472420  2/1973  Australia.

Primary Examiner—Janyce Bell
Attorney, Agent, or Firm—Roylance, Abrams, Berdo & Goodman, L.L.P.

[57] ABSTRACT

A plurality of petri dishes or other glass or plastic containers are coated on the inside bottom surface of the containers by passing the containers through a coating or layering apparatus. The apparatus includes an indexing conveyor to sequentially pass the open containers through a filling station where an amount of a coating material is applied while tilting the container to one side thereby distributing the material to the entire bottom surface of the container. The containers are conveyed to an aspirating station to aspirate excess material while tilting the container toward the aspirating nozzle. Subsequent to the aspiration step, the containers are tilted in the opposite direction to distribute the material in the container. The material is then dried and the containers stacked and packaged. The coating material includes metal ions such as calcium or other divalent metal ions, in a suitable carrier that is able to bond the bottom inside surface of the container. The coating material forms a dehydrated, solidified layer bonded onto the bottom surface of the container. The coating material can be a water/agar solution or a plastic resin in an appropriate solvent containing the calcium ions.

41 Claims, 7 Drawing Sheets

METHOD AND APPARATUS FOR COATING CONTAINERS

FIELD OF THE INVENTION

The present invention is directed to a method and apparatus for coating containers and in particular coating petri dishes with an agent for inducing gelling of a nutrient growth medium. The invention is particularly directed to forming a substantially dry, stable coating or layer of a gel inducing agent in or on the bottom of a container which becomes incorporated as part of a nutrient growth medium.

BACKGROUND OF THE INVENTION

Numerous devices are known in the art for filling containers with a predetermined amount of material. Other devices are known for coating the inner surfaces of containers. These devices can produce acceptable results for certain materials but do not universally produce good results for all coating materials.

Producing a stable layer of gelling or gel inducing agent in a petri dish is typically time consuming and difficult. Accurate test results require a uniform and sterile layer of the gelling agent on the petri dish. Commercial production of coated petri dishes often require manual handling of the dishes which produces inconsistent results and increased risk of contamination. One example of previous nutrient base medium applies a gelling agent consisting of a coating of calcium chloride and agar solution on the dish followed by a liquid gelling nutrient layer of, for example, low methoxyl pectin. This method requires a complete and uniform coating of the calcium chloride to prevent delayed or incomplete gelling of the pectin. This approach often produced unsatisfactory results for general applications. For example, it is necessary to ensure that the total surface area of the plate is covered with both the pretreatment layer of the gelling agent and the growth medium. Failure to cover the plate completely results in incomplete gelling of the medium and inaccurate test data.

Other methods for preparing petri dishes use a pectin gel having an agar gel layer containing calcium chloride. In this prior method, about six milliliters of a 1% agar solution containing about 100 milligrams of calcium chloride is dispensed into a petri dish which was previously sterilized. The petri dish is then rocked hand and swirled to spread the layer uniformly over the bottom of the dish. The dish is then placed on a level surface and allowed to cool and gel. The cooled and gelled dishes are stacked in a clean room and allowed to temper and cure. After six to eight days of tempering, the treated dishes are examined for contamination and sorted for packaging. The packaged dishes are then stored in a cool, dry location for an additional seven to 14 days and reexamined for contamination. Any contaminated dishes are discarded and the remaining dishes are packaged for shipment.

The above-noted procedure experiences numerous drawbacks in addition to the laborious nature of the procedure. For example, this procedure often results in condensation forming on the lid of freshly layered dishes which needs to be removed before storage. The repeated handling of the dishes and the static charge of plastic plates produces significant mold contamination of the gel layer in spite of the efforts to maintain temperature controlled and clean, sterile rooms. The process further requires large amounts of storage space for the two week tempering period thereby increasing manufacturing costs.

The prior methods of producing coated petri dishes typically result in unacceptable moisture levels in the coating material rendering the layer susceptible to freezing temperatures during shipping, thereby destroying the layer. The temperature fluctuations during shipping and storing result in the formation of condensation within the dishes and the sleeves holding the dishes. The manual procedure for coating the dish requires care to ensure complete coverage of the bottom of the dish without spillage or bubble formation in the layer. Failure to maintain a level surface during the hardening of the coating or disturbing the dish during hardening produces a layer that is not smooth and flat. An uneven layer of the coating material produces poor qualitative and quantitative results in the finished product.

Several growth media and methods of preparing petri dishes are known in the art. Examples of previous methods and devices are generally disclosed in U.S. Pat. No. 4,170,861 to Snyder et al., U.S. Pat. No. 4,565,787, U.S. Pat. No. 3,928,136 to Launey, U.S. Pat. No. 4,988,302 to Smith et al., U.S. Pat. No. 5,089,413 to Nelson et al., U.S. Pat. No. 4,656,130 to Shoshan, and U.S. Pat. No. 4,262,091 to Cox. These devices and methods have met with limited success and have not provided a completely satisfactory result. There is accordingly a continuing need in the art for a method and apparatus for efficiently producing a treated petri dish containing a thin coating layer.

SUMMARY OF THE INVENTION

The present invention is directed to a method and apparatus for forming a layer of a coating material in a container. In particular, the invention pertains to a method and apparatus for preparing a layer of a coating material on the bottom of a petri dish.

Accordingly, a primary object of the invention is to produce a stable layer of a coating material in a petri dish in an efficient and rapid manner. A further aspect of the invention is to produce a fully automated apparatus for receiving a plurality of containers and producing a coating on the bottom surface of each container.

A further object of the invention is to provide a thin, uniform coating of a gel inducing agent capable of solidifying a gel-forming nutrient material in a petri dish.

The container, such as a presterilized petri dish, is initially separated from its lid and passed through a sterilizing chamber to maintain the sterility of the dish. Typically, the sterilizing chamber directs filtered air onto the container in combination with a sterilizing agent such as germicidal ultraviolet light. The dish is then filled with a predetermined amount of a coating material, such as a base medium containing metallic ions plus a gel inducing agent. In embodiments, the dish is tilted to distribute the material across the bottom of the container. The container is tipped to one side and the excess coating material is removed, preferably by aspiration. After removing the excess material, the container is tilted in the opposite direction to uniformly distribute the remaining coating material. The coated dish is then cooled to form a gelled coating and then passed through a dehydrating or drying chamber directing heated air onto the container to dehydrate the coating material. In embodiments, the coating material is a gel-forming material containing a gel inducing agent and the drying air is heated to remove moisture from the coating material.

The method of the invention produces a thin uniform coating which is thinner than conventional coatings. The resulting coating is dry and stable and can be shipped and stored for extended periods of time without the formation of detrimental condensation or cracks and without danger of freezing, or growth of contaminants.

The apparatus for use in the invention is preferably a fully automated apparatus capable of providing continuous production of the coated containers. In embodiments, the apparatus accepts a plurality of containers and the associated lids. The lids are separated from the container and sequentially indexed through a number of processing stations and then reassembled. The containers are first passed through a sterilizing station and then to a filling station. Excess coating material is then removed from the container in at least one and preferably two aspiration stations followed by a tilting station to tilt and uniformly distribute the remaining coating material. A gelling station directs cool air onto the coated containers followed by heated air in a second sterilizing and drying chamber to dry the coating. When the coating reaches the desired dryness, the lids are automatically replaced onto the container.

These and other aspects of the invention are basically attained by providing an apparatus for forming a layer of a coating material in a container, the apparatus comprising conveyor means for conveying the container through the apparatus; filling means for filling the container with an amount of the coating material; first aspiration means for aspirating a portion of the coating material from the container; and dehydrating means for dehydrating said coating material to form a substantially uniform coating of said coating material in said container.

These aspects of the invention are also attained by a method of producing a coating of a coating material on the inside bottom surface of a container comprising the steps of filling said container with an amount of a coating material in a filling station of a conveyor assembly; removing an excess of the coating material from said container to form a coating of the coating material, and dehydrating the coating of the coating material in the container to form a uniform and stable coating. A thin layer of the coating material adheres over the entire surface due to surface tension and cohesive properties of the coating material.

These and other objects, advantages and salient features of the invention will become apparent from the following detailed description, which, taken in conjunction with the annexed drawings, discloses preferred embodiments of the invention.

BRIEF DESCRIPTION OF THE DRAWINGS

Referring to the drawings which form a part of this original disclosure in which.

DETAILED DESCRIPTION OF THE INVENTION

Figure 1:
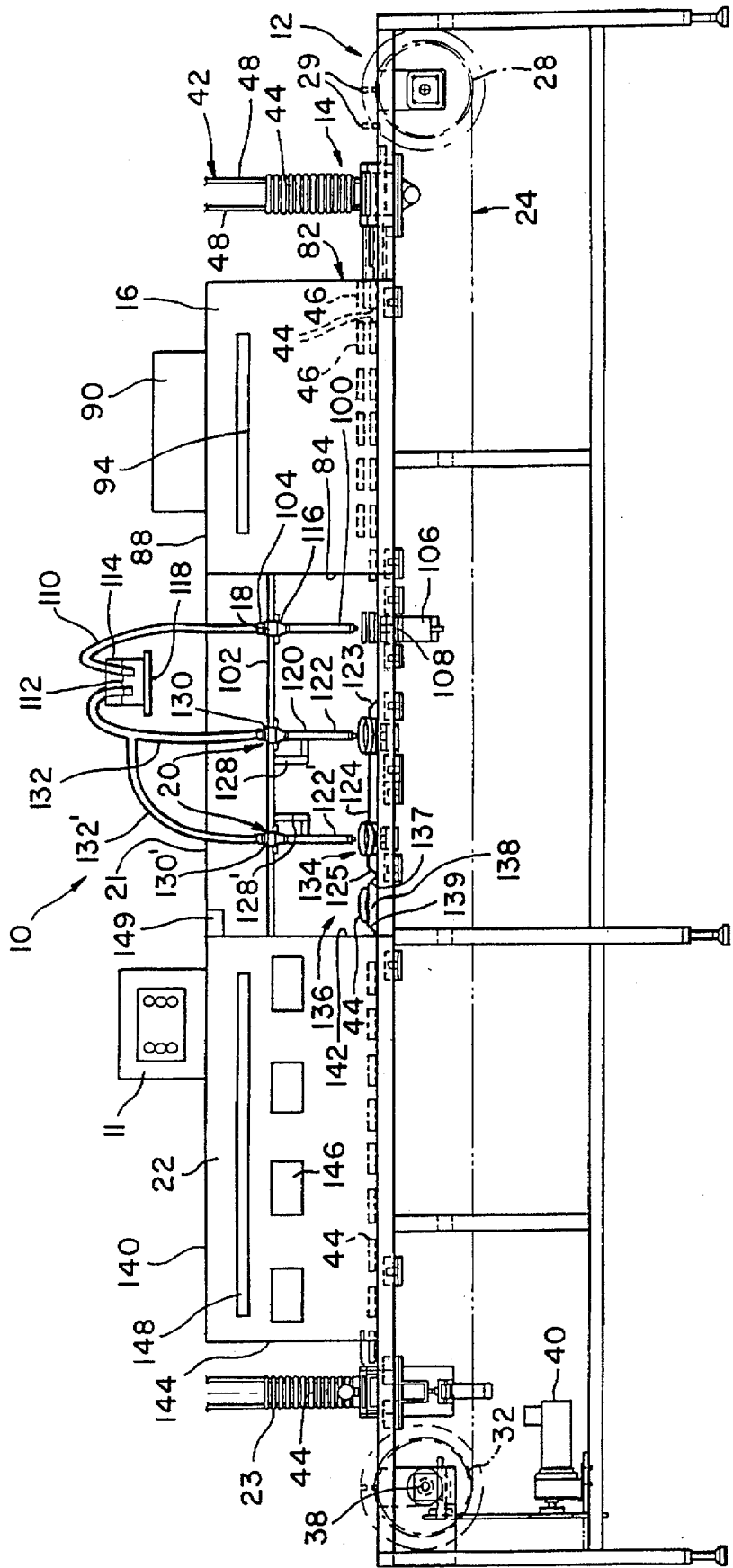
FIG. 1 is a side elevational view of the apparatus in accordance with a preferred embodiment of the invention.

The present invention relates to a method and apparatus for producing a uniform coating or layer of a material on the inside bottom surface of a plastic or glass container. The method and apparatus are particularly suitable for forming a uniform coating or layer of a gellable cohesive or adhesive material in a container. A preferred form of the invention forms a thin coating or layer of gelled medium in a plastic or glass petri dish.

The method and apparatus are suitable for producing a thin layer of a coating material in a variety of containers. In preferred embodiments of the invention, the container being coated is a standard petri dish typically used to propagate and quantify microbiological cultures. The coating material can be a solid support medium capable of supporting the growth of a biological sample. In preferred embodiments, the coating material is a material capable of forming a gel layer when cooled on the bottom surface of the petri dish and includes a gel inducing agent. In one embodiment, the gel layer contains a sufficient amount of calcium ions to cause a nutrient medium containing pectin to form a gel when placed in the container.

The method and apparatus of the invention are particularly suited for forming a uniform layer of a gelled material containing a uniform distribution of a metal cation, such as calcium cations. A nutrient-containing material including, for example, a low methoxyl pectin gel-forming material, is poured into the coated petri dish. The uniform distribution of the cation forms a uniform gelled nutrient base layer.

In preferred embodiments, the coating material is a gel-forming solution containing calcium chloride as a gel inducing agent such as the composition disclosed in U.S. Pat. No. 4,282,317 which is hereby incorporated by reference in its entirety. As discussed therein, a solid medium is made by first applying a coating of a material which contains a source of calcium ions such as calcium chloride. Thereafter, a pectin solution containing the essential growth supporting nutrients is poured over the first layer so that the calcium ions react with the pectin to form a gel layer.

A suitable aqueous coating solution contains about 2% (2 grams per 100 milliliters deionized or distilled water) agar-agar and calcium chloride. Other compounds containing multivalent metal cations can be employed, as well known in the art, to provide sufficient gelling of pectin. Typically, the calcium compounds include, for example, calcium chloride, calcium nitrate and calcium phosphate. In preferred embodiments, the calcium compounds are water soluble capable of providing a source of calcium ions to react with and gel the pectin. The concentration of the calcium chloride or other multivalent metal cation providing compound is determined to provide the proper metal cation concentration to cause solidification of the nutrient-pectin composition when poured onto the layer containing metallic gel inducing ions.

A solution of a 2% agar and metal cation-providing material is prepared by suitable means such as, for example, by dissolving the agar and metal salt in heated water at 15 pounds pressure and about 121° C. in an autoclave. The sterile agar mixture can then be dispensed to the petri dish to cover the bottom of the dish as discussed hereinafter in greater detail.

In embodiments of the invention, the coating material contains at least about 7 grams of calcium chloride per 100 milliliters of the water/agar mixture. Preferably, the coating material comprises calcium chloride, agar and water. In alternative embodiments, the gelling component may be, for example, gelatin, silica gel, Carrageenan gum or other gums. Other materials can also be used as the carrier for the multivalent cation providing compound. In one embodiment, the coating material is a plastic resin material dissolved or dispersed in an appropriate solvent or mixture of solvents containing an effective amount of calcium ions so that the mixture bonds with the container. When a plastic container is used, the plastic resin of the coating material is selected to be compatible with the container to adhere to the bottom wall of the container. The coating material includes a plastic resin and a metal ion concentration so that a sufficient amount of the metal ions are available for gelling a pectin-containing solution. In further embodiments, additional resins or carrier types can be used to provide calcium ions available for gelling a pectin material. The carriers are inert and nontoxic to living cells and should not be hydrolyzed during the process. Generally, the coating material does not include growth nutrients. However, in embodiments of the invention, the coating material can contain various nutrients to support biological growth as known in the art.

The liquid growth medium which is poured onto the calcium cation layer can contain a low methoxyl pectin and a variety of other constituents. In general, the medium can correspond to a wide variety of growth media as known in the art for microbial cell and/or tissue cultures, except to the extent that components which break down or interfere with the pectin should be avoided. Typically, the culture medium includes several other constituents including a carbon source such as glucose or other sugars, a nitrogen source, and other micronutrients in the form of natural products such as tryptone, peptone, beef extract, yeast extract, etc. or synthetic materials. The actual composition of the growth medium will depend to a large extent on the particular culture being tested. The carbon source is generally included in the amount of about two to about 10 grams per liter of solution. The nitrogen source is included in the amount of about two to about 10 grams per liter of solution.

The method and apparatus are particularly effective for applying a thin coating on the inside bottom surface of a container with a material capable of gelling at room temperature. The coating material is preferably heated until liquid and applied to the bottom of the container as a solution and allowed to cool and gel.

In a preferred form of the invention, the coating material is an aqueous solution of a metal salt such as calcium chloride and a non-nutrient gel forming material. The non-nutrient gel forming material is preferably a low methoxyl pectin which can solidify at room temperature. The metal salt is a gelling agent capable of gelling a nutrient base medium such as a medium containing low methoxyl pectin. The method and apparatus of the invention are particularly adapted for forming a stable layer of the metal ion providing source and the non-nutrient gel-forming material. A nutrient base medium is then poured onto the layer of the gelling agent to solidify the nutrient base medium.

Referring to the drawings, the method of the invention utilizes the apparatus 10 adapted for continuously handling a plurality of petri dishes simultaneously. The apparatus 10 is fully automated by a microprocessor control 11 to sequentially index the petri dishes through the various treating stations. The apparatus is capable of receiving a plurality of petri dishes, automatically separating the lids, coating the inside dish bottom and replacing the lid on the dish. As shown in FIGS. 1–9, the apparatus essentially comprises a conveyor assembly 12, a destacking unit 14, a first sterilizing chamber 16, a dispensing station 18, an aspirator unit 20, a dehydrating, drying and sterilizing chamber 22 and a restacking unit 23. In operation, the apparatus 10 receives a plurality of petri dishes 44 in destacking unit 14 in a stacked relationship. The petri dishes 44 are placed in the destacking unit 14 with the associated lid 46. The destacking unit 14 separates the lid 46 from the dish 44 at the bottom of the stack and places the dish 44 and lid 46 on parallel indexing conveyors 24, 26, respectively. The dish 44 and lid 46 are passed through the apparatus 10 in a stepwise fashion to the various stations. Initially, the dishes 44 and lids 46 are passed through the sterilization chamber 16 which subjects the dish 44 and lid 46 to sterile air and germicidal ultraviolet light.

The dish 44 is then conveyed to the dispensing station 18 where the dish 44 is stopped and a dispensing nozzle meters a predetermined amount of the coating material into the dish 44. In embodiments of the invention, the nozzle dispenses the coating material along a first side of the dish while a pneumatic plunger slowly lifts the first side of the dish to a tilted position thereby causing the material to flow across the bottom of the dish. The pneumatic plunger is retracted whereby the dish is returned to a level position and advanced to aspirator unit 20.

In aspirator unit 20, the dish 44 is tilted toward the first side to pool the coating material dispensed by the dispensing nozzle. An aspirator nozzle in a first aspirating station is lowered into the pooled material to remove the excess material. In preferred embodiments, the dish is indexed to a second aspirating station and a second aspirator nozzle is lowered into the dish to remove any remaining pooled material while keeping the dish in the tilted position.

After removing the excess coating material, the dish is advanced to a tilting station where the dish is tilted in the opposite direction to cause the residual pooled material not removed in the aspiration step to flow away from the first side and spread uniformly over the bottom of the dish. The dish is then returned to the horizontal position, passed under cooling fans 149, and advanced to drying chamber 22.

Dehydrating chamber 22 directs warm air onto the dish to remove excess moisture. In preferred embodiments, the temperature of the drying air is below the remelting temperature of the coating material. Dehydrating chamber 22 further subjects the dish and the lids to ultraviolet light to maintain the dish and coating material in a sterile condition. The dishes exit dehydrating chamber 22 in a substantially dehydrated condition containing a solid layer with gel inducing ions.

The dishes 44 and the lids 46 are next advanced to a restacking unit where the lids are placed on the respective dish. The dishes and lids are then pushed upward into a stacking unit where the coated dishes are removed and packaged.

Figure 2:
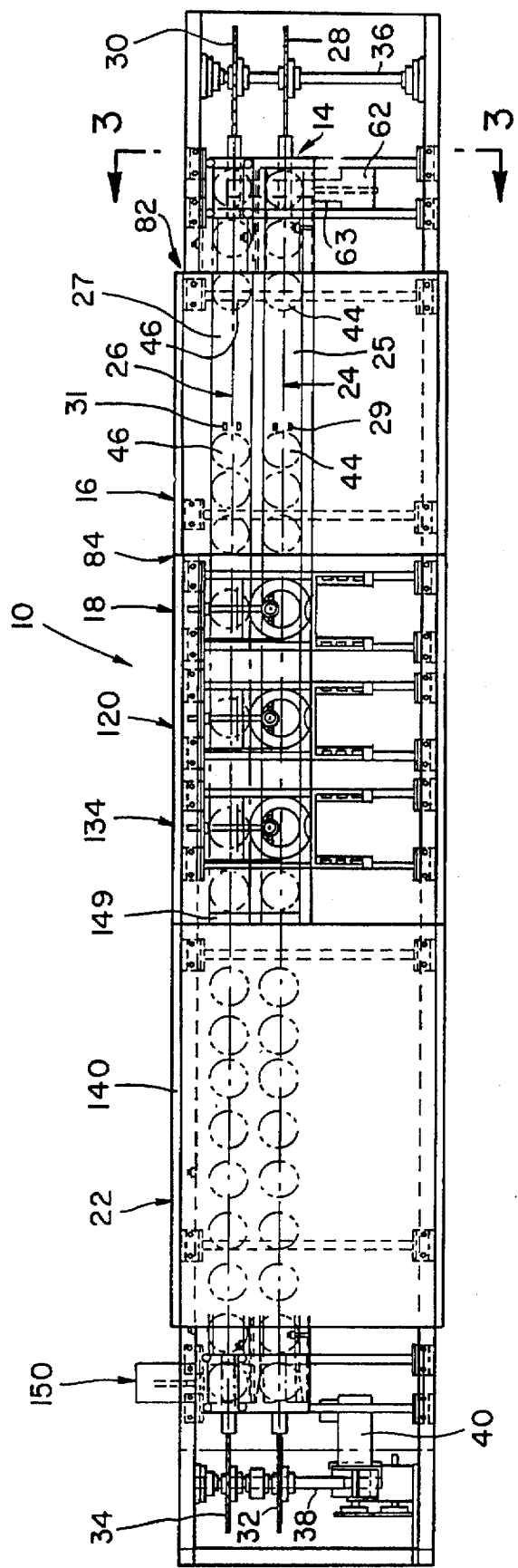
FIG. 2 is a top plan view of the apparatus of FIG. 1 showing the destacking device, sterilizing chamber, filling station, aspiration station, drying and sterilizing chamber and restacking device.

As shown in FIG. 2, apparatus 10 includes first and second parallel indexing conveyors 24, 26 in the form of parallel chains passing over sprockets 28, 30 at a leading end and drive sprockets 32, 34 at the discharge end. Sprockets 28, 30 are mounted on a common rotating shaft 36. Drive sprockets 32, 34 are mounted on a common drive shaft 38 which is connected to a drive motor 40 by appropriate transmission or gear connections. Drive motor 40 is preferably a step motor operated by a microprocessor to advance chains 24, 26 in an indexing or step-wise manner through each station as discussed hereinafter in greater detail.

Sprockets 28, 30, 32, 34 are fixed to shafts 36, 38 to rotate and advance chains 24, 26 in an identical manner. As shown, the leading sprockets 28, 30 are the same size and the drive sprockets 32, 34 are the same size so that the chain conveyors 24, 26 move at the same speed and the same distance with each revolution of the sprockets. Chain conveyors 24, 26 advance along horizontal conveying surfaces 25, 27, respectively, which extend the full length of the apparatus 10.

Figure 3:
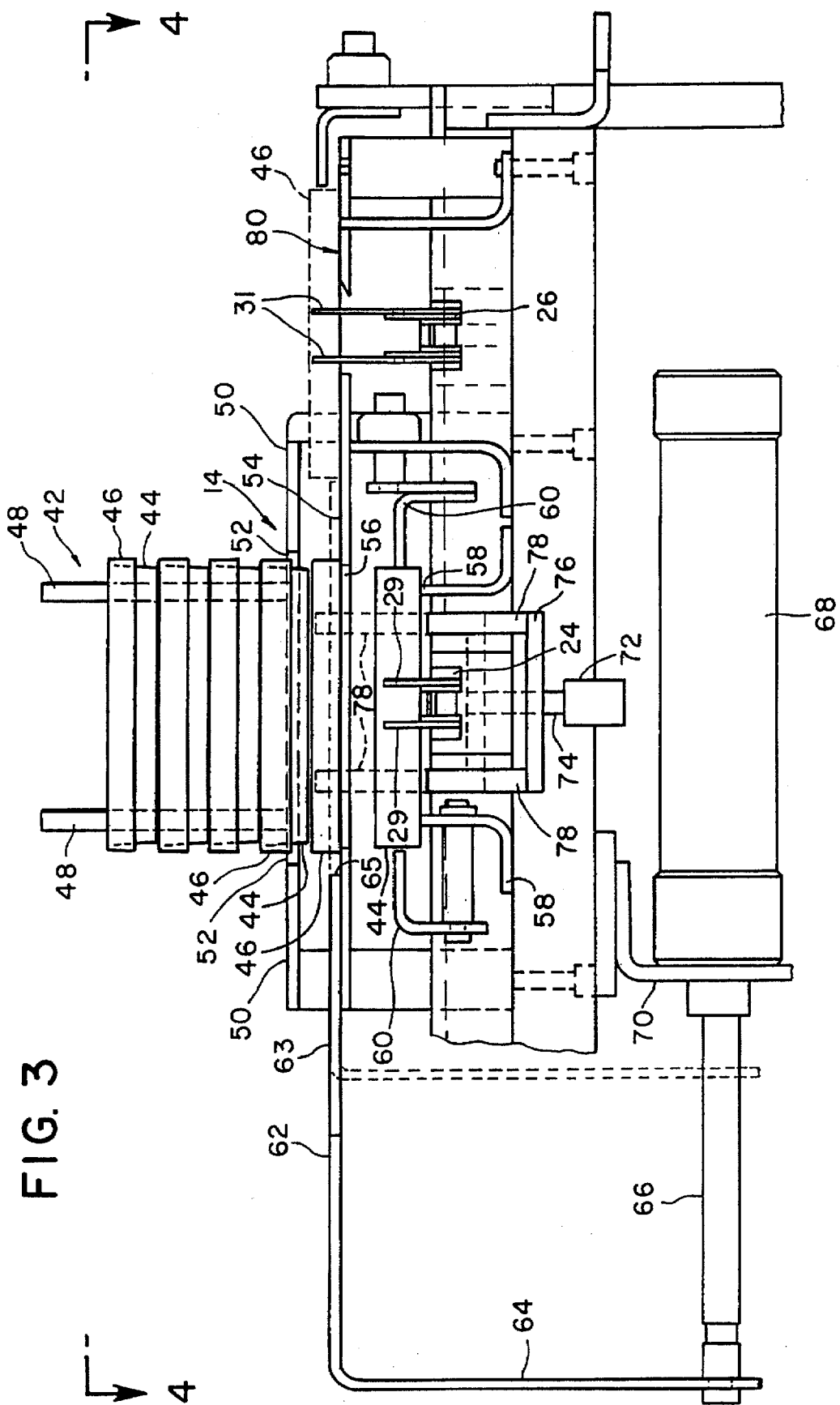
FIG. 3 is a partial cross-sectional view of the destacking device taken along line 3—3 of FIG. 2.

Conveyor chains 24, 26 include a plurality of spaced-apart pushing bars 29, 31 extending upwardly from the conveying surfaces 25, 27, respectively, for defining a conveying area and for engaging the petri dishes 44 and lids 46. The pushing bar 29 coupled to conveyor chain 24 extends upwardly a distance approximately equal to the upper edge of the petri dish being conveyed along the conveying surface 25. Conveyor chain 26 extends along a conveying surface 27 parallel to the conveying surface 25 of the conveyor chain 24. As shown in FIG. 3, the conveying surface 27 of conveyor chain 26 is elevated from the conveying surface 25 of conveyor chain 24 such that the conveying surfaces of the petri dish and lid are parallel but in different planes. The pushing bar 31 of conveyor chain 26 is longer than the pushing bar 29 of conveyor chain 24 to extend upwardly to the conveyor surface 27 a distance sufficient to convey the lid 46.

Figure 4:
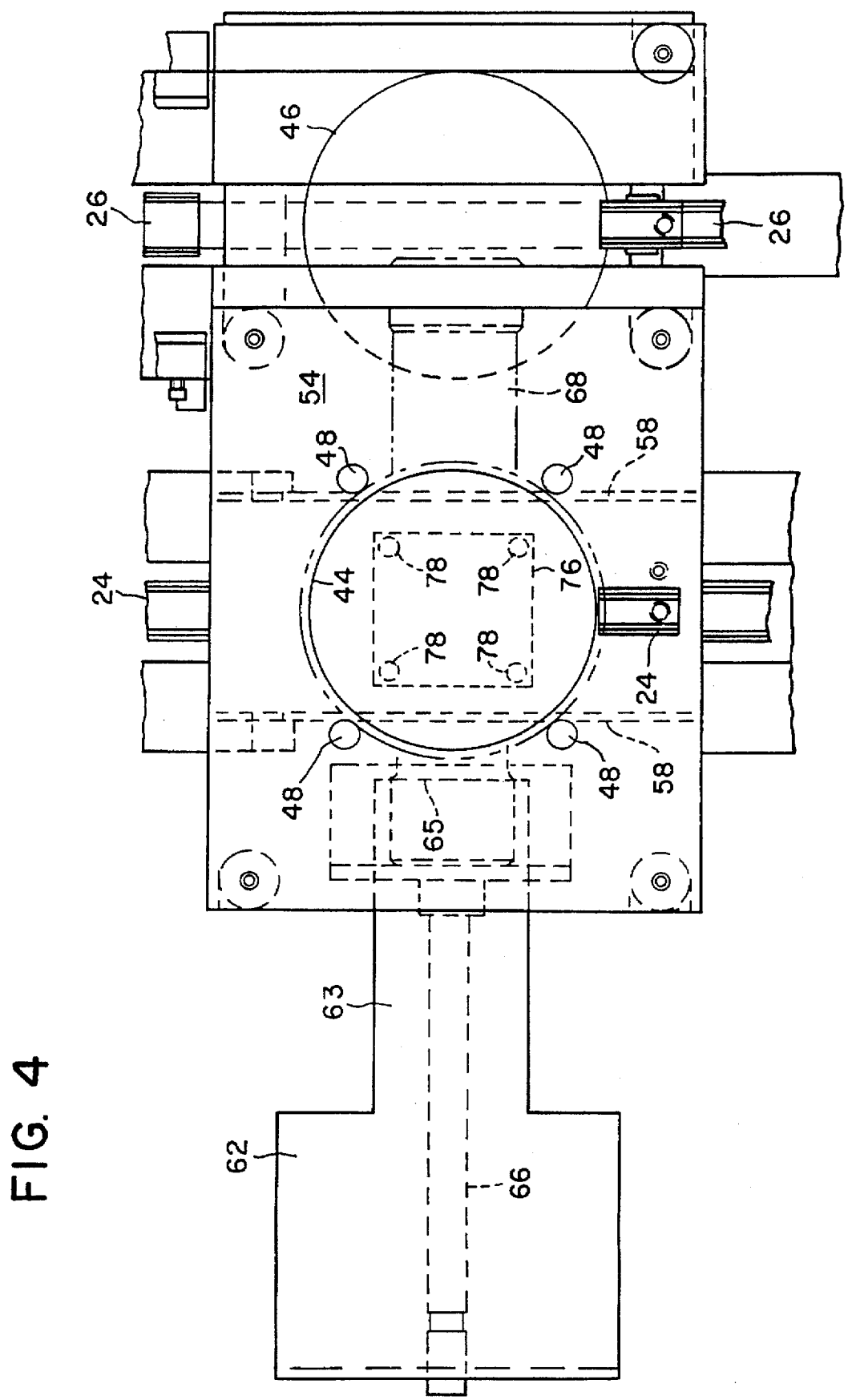
FIG. 4 is a partial top plan view of the destacking device as viewed along line 4—4 of FIG. 3.

Destacking device 14 as shown in FIGS. 3 and 4 includes a stacking rack 42 for receiving a plurality of petri dishes 44 and associated lids 46. Stacking rack 42 in preferred embodiments includes four vertical stacking rods 48 spaced apart to maintain the dishes in a vertical stack. Rods 48 as shown in FIG. 3 extend upwardly from an upper plate 50 having an aperture 52 dimensioned to allow dishes 44 and lids 46 to pass vertically therethrough. A lower slide plate 54 is spaced below and parallel to upper plate 50. Slide plate 54 is also provided with an aperture 56. In preferred embodiments, aperture 56 has a slightly oval shape and is dimensioned to permit dish 44 to pass through while lid 46 remains on slide plate 54. Positioned below slide plate 54 is first chain conveyor 24 cooperating with horizontal conveyor slide surface 58 and parallel side guide rails 60. As shown in FIG. 3, slide plate 54 extends over both chain conveyors 24, 26 and forms part of the conveying surface of chain conveyor 26.

A slide arm 62 is arranged for sliding movement on slide plate 54. Slide arm 62 includes a connecting arm 64 coupled to a piston rod 66 extending axially from pneumatic piston 68. As shown in FIG. 3, piston 68 is mounted to the bottom of the frame 70 of conveyor assembly 12. In alternative embodiments, piston 68 can be mounted by an independent support.

Also mounted on frame 70 is a second pneumatic piston 72 having piston rod 74 mounted for vertical reciprocating movement. A reciprocating square plate 76 is coupled to the distal end of piston rod 74. As shown in FIG. 3, four upwardly extending rods 78 are mounted on the four corners of plate 76. Two of the rods 78 are positioned on one side of chain conveyor 24 while the other two rods are positioned on the opposite side of chain conveyor 24. Plate 76 is mounted perpendicular to the piston rod 74 while the rods 78 are perpendicular to plate 76.

As shown in FIG. 4, slide arm 62 includes a narrow tongue portion 63 extending forward to define the leading end 65. Tongue portion 63 has a width less than the spacing of rods 78 so that rods 78 do not interfere with the slide arm 62. In this manner, rods 78 can be extended upward past slide arm 62 as shown in phantom lines of FIG. 3 when slide arm 62 and piston rod 66 are in the retracted position.

Pneumatic pistons 68 and 72 are connected to and actuated by a central microprocessor 11 to activate the pistons 68, 72 in a controlled manner and in cooperation with the step-wise advancing movement of chain conveyor 24. In operation, a plurality of petri dishes and their associated lids are stacked in stacking rack 42. Piston 72 extends rod 74 upwardly whereby rods 78 are in an upward position, as shown in phantom lines, lifting petri dish 44 a slight distance off surface of slide arm 62. Piston 68 is actuated by the microprocessor 11 to extend piston rod 66 whereby slide arm 62 is withdrawn to the position shown in FIG. 3. Piston 72 retracts, gently lowering dish 44 through opening 56 in slide plate 54 and onto slide plate surface 58 of chain conveyor 24. Lid 46 of the associated petri dish 44 is retained on slide plate 54 with the plurality of petri dishes and lids in stacking rack 42 resting on lid 46. Piston 68 is then actuated by the microprocessor to retract piston rod 66 whereby slide arm 62 pushes lid 46 over slide plate 54 to a second slide surface 80 of chain conveyor 26 as shown in phantom lines of FIG. 3. As lid 46 is pushed from under the plurality of petri dishes and lids in stacking rack 42, the plurality of petri dishes fall onto the surface of slide arm 62. Chains 24, 25 then advance forward an incremental amount so that the next conveying area is positioned below the destacking device. Piston 72 is then activated whereby rods 78 lift the next petri dish in the stack from the surface of slide arm 62. It is desirable to have rods lift the stack of petri dishes from slide arm 62 before slide arm 62 moves to the position shown in FIG. 3 to prevent the dishes from falling or becoming twisted in the stack and to lower the plates through the opening in a level manner. Piston 68 is then activated to withdraw slide arm 62 from stacking rack 42 to the position in FIG. 3. The actuation cycle of pistons 68, 72 and chains 24, 26 is again performed.

Referring to FIGS. 1 and 2, chain conveyors 24, 26 are advanced in incremental steps to convey the petri dishes 44 and their associated lids 46 simultaneously from destacking device 14 through sterilizing chamber 16 in a step-wise manner. In this manner, the lid 46 is parallel to the petri dish 44 throughout the advancing movement as shown in FIG. 2. Sterilizing chamber 16 is a closed chamber having an inlet 82 where the chain conveyors 24, 26 and petri dishes 44 and lids 46 enter at an upstream end. An outlet 84 is provided at a downstream end where the chains 24, 26, petri dishes 44 and lids 46 exit.

Sterilization chamber 16 can include an observation window in housing 88. A fan 90 is included to provide a constant flow of sterile air to the chamber to provide positive pressure within the chamber. An ultraviolet light source 94 floods the interior of sterilizing chamber 16 to provide a sterilizing and germicidal treatment. The ultraviolet light source can be a standard UV source having an intensity sufficient to provide a germicidal affect on the petri dishes and their lids. The length of sterilization chamber 16 is selected to provide sufficient sterilizing effect for the operating speeds of the chain conveyors. In further embodiments, the intensity or amount of the UV source can be adjusted in relation to the advancing speed of chain conveyors 24, 26. In alternative embodiments, other sterilization devices may be used such as, for example, gamma radiation or sterilizing gas treatments.

Outside air is drawn through an HEPA filter and introduced as sterile air into chamber 16 to maintain a positive pressure within chamber 16. The positive pressure in chamber 16 creates an air flow directed outwardly through dish inlet 82 to prevent outside air from entering the dispensing station 18 which can carry contaminants such as bacteria or spores.

As shown in FIG. 1, chain conveyors 24, 26 and the petri dishes 44 and lids 46 exit sterilization chamber 16 and sequentially advance to dispensing station 18. Dispensing station 18 includes a dispensing nozzle 100 coupled to a support brace 102. In embodiments of the invention, dispensing nozzle 100 is in a fixed position a short distance above the petri dish 44. An optional pneumatic cylinder 104 is connected to and operated by a microprocessor 11 to lower nozzle 100 downwardly toward the advancing petri dishes and to raise nozzle 100 at the end of the filling cycle.

Nozzle 100 is supplied with fluid material 112 by a pump 116 and flexible supply tube 110 extending from a closed storage vessel 114. Storage vessel 114 can be any suitable flask or other container capable of storing fluid material in a sterile condition. Typically, vessel 114 is provided with a suitable closure member to prevent contamination of the contents. In embodiments where the fluid material is a gel-forming material, a warming plate 118 is included to maintain the material in a flowable condition. In preferred embodiments, pump 116 is a standard peristaltic pump, although other pump apparatus can be used.

Pump 116 is connected to microprocessor 11 to control the amount of material being dispensed and the timing of the dispensing cycle. Positioned below chain conveyor 24 is a second pneumatic cylinder 106 and plunger 108 as shown in FIG. 5.

In operation, petri dishes 44 are advanced to dispensing station 18 and stopped below dispensing nozzle 100. As shown in FIG. 1, dispensing station 18 and aspiration station 20 are enclosed within an enclosure 21, such as clear plastic, to reduce the risk of contamination of the dishes 44 during filling. Nozzle 100 preferably is positioned a slight distance above petri dish 44. Pump 116 is then actuated to introduce a predetermined amount of the fluid material into the petri dish 44.

Figure 5:
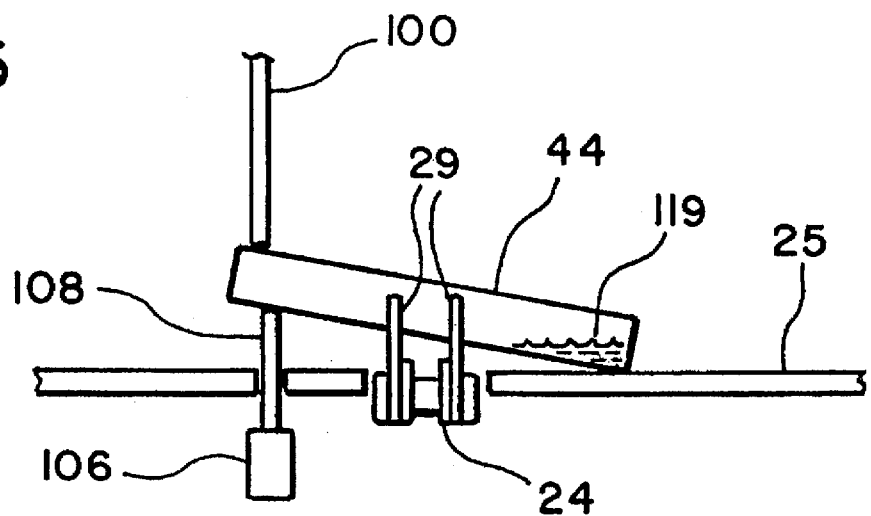
FIG. 5 is a partial cross-sectional view of the filling station showing the dispensing nozzle and the pneumatic tilting device.

In one embodiment of the invention as shown in FIG. 5, dispensing nozzle 100 is positioned toward one edge of the petri dish along the side wall. As dispensing nozzle 100 introduces the fluid material into petri dish 44, the pneumatic cylinder 106 is actuated and plunger 108 lifts one edge of the petri dish upward. As shown in FIG. 5, pneumatic cylinder 106 is positioned below dispensing nozzle 100 so that plunger 108 tilts petri dish 44 away from the point where the dispensing nozzle 100 introduces the fluid material. As petri dish 44 is tilted, the fluid material flows across the bottom of the petri dish to ensure the bottom surface is completely coated. The excess fluid material forms a pool 119 on the side opposite the dispensing nozzle 100. When the desired amount of fluid material is introduced to the petri dish 44, the pneumatic cylinder 106 is again activated and plunger 108 is retracted to lower petri dish 44 to the initial horizontal position whereby the fluid material spreads across the bottom surface of the dish. Chain conveyors 24, 26 are again actuated to advance the filled petri dish to the aspiration station 20 and bring a new petri dish into position for filling. In alternative embodiments, the fluid material is dispensed into the dish 44 without tilting the dish 44.

Pump 116 is controlled by a microprocessor to dispense the amount of fluid material in a predetermined amount. The amount of fluid material dispensed into the petri dish 44 is the minimum amount necessary to completely cover the bottom surface of the dish. In preferred embodiments, an excess of the fluid material necessary to cover the bottom of the dish is dispensed. The dispensing of the fluid material is controlled by the microprocessor which determines the speed and duration of the pump cycle. Generally, the pump speed and operating time cycle are coordinated to dispense the selected amount of the fluid material. In alternative embodiments, the nozzle 100 includes a solenoid actuated dispensing valve with the supply line being fed under constant pressure. In this embodiment, the dispensing valve is actuated by the microprocessor for a selected time cycle to dispense the fluid material.

Figure 6:
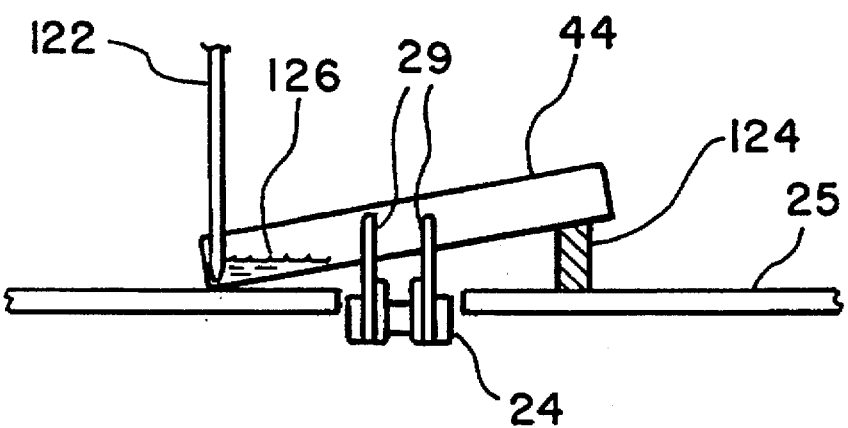
FIG. 6 is a partial cross-sectional view of the aspiration station showing the aspirating nozzle and pneumatic tilting device.

Once the petri dish 44 is filled and pneumatic cylinder 106 is retracted, the petri dish is advanced to the first aspiration station 120. A first aspiration nozzle 122 is lowered into contact with the fluid material to aspirate the excess fluid material from the petri dish 44 and return the fluid material to the storage vessel 114. The horizontal sliding surface 25 of the conveyor assembly 10 includes a lifting cam surface 124. The advancing movement of the chain conveyor 24 causes one edge of the bottom face of the petri dish 44 to engage and ride up the inclined surface 123 of the cam 124 thereby causing the petri dish to tilt to one side as shown in FIG. 6. In preferred embodiments, cam 124 tilts petri dish in the opposite direction from the tilting direction at the dispensing station 18. In this manner, the fluid material in the petri dish flows back toward the initial feed location to ensure complete coverage across the bottom of the petri dish 44. The excess fluid material collects in a pool 126 on the side opposite the cam 124. While the petri dish 44 is in the inclined position shown in FIG. 6, aspiration nozzle 122 is lowered into the pool 126 to remove an excess of the pooled fluid material.

Aspiration nozzle 122 is operated by a pneumatic cylinder 128 which raises and lowers nozzle 122 into contact with the petri dish 44 and the fluid material 126 therein. The actuation of the pneumatic cylinder 128 is controlled by the microprocessor to coordinate the aspiration operation with the advancing movement of each petri dish 44. A suitable pump 130, such as a standard peristaltic pump, is connected to nozzle 122 to aspirate the fluid material from the petri dish and return the fluid material through a return line 132 to the supply container 114. The pump 130 is also connected to and operated by microprocessor 11 to coordinate the aspiration with the advancement of the petri dish 44.

In preferred embodiments of the invention, a second aspiration station 134 is provided downstream of the first aspiration station 120. Preferably, cam surface 124 extends the length of the first and second aspiration stations 120, 134 so that the petri dish 44 is advanced by the chain conveyor in the inclined position similar to that shown in FIG. 6. A second aspiration nozzle 122' connected to a pneumatic cylinder 128? and return line 132' are provided in a similar arrangement as in the first aspirating station 120. Aspiration nozzle 122' is also connected to a pump 130'. Pump 130' and pneumatic cylinder 128' are similarly connected to a microprocessor to coordinate the aspiration of the fluid material with the forward advance of the petri dish 44. Since the petri dish 44 advances to the second aspiration station 134 in the inclined position, the excess fluid material not removed in the first suction station remains pooled in the lower portion of the petri dish. Second aspiration nozzle 122' is lowered into contact with any remaining fluid material in the petri dish 44 whereby pump 130' is actuated to aspirate the fluid material from the petri dish 44 to the supply vessel 114.

Figure 7:
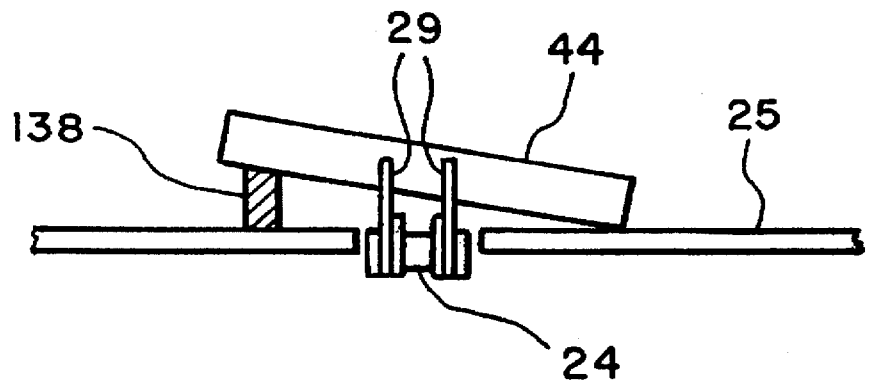
FIG. 7 is a partial cross-sectional view of the tilting device.

As shown, the downstream end of cam 124 has a declining surface 125 which gently lowers the petri dish 44 to the horizontal position on the conveying surface 25 as the chain conveyor 24 advances the petri dish 44 forward. Immediately thereafter, the petri dish 44 is advanced to a tilting station 136. The petri dish 44 engages a second cam surface 138 having an incline 137 positioned on the horizontal slide surface 25 of conveyor 24. The cam surface 138 is positioned to engage the bottom of the petri dish 44 along one edge to tilt the petri dish 44 as shown in FIG. 7. In preferred embodiments, cam 138 tilts the petri dish in a direction opposite the direction of tilt during the aspiration steps. In this manner, the fluid material remaining in the petri dish 44 flows back across the bottom of the surface to produce a thin, uniform layer of the fluid material. The petri dish 44 is maintained in the tilted position for a selected time period to ensure uniform coverage of the fluid material on the bottom. Cam 138 includes a declining surface 139 at the downstream end to return the petri dish 44 to the horizontal position on conveying surface 25. The tilt provided by the cam 138 alternatively can be supplied by a pneumatic lift at that station.

Prior to entering the heated drying chamber 22, a flow of cool sterile air is directed onto the coated petri dish 44 to gel the fluid material when a gellable material is present. Cool air is directed downwardly from blower 149 as shown in FIG. 2.

The petri dish 44 and the coordinated lid 46 are then advanced through the dehydrating chamber 22. As shown in FIG. 1, the dehydrating chamber is a closed housing 140 having an inlet opening 142 and an outlet opening 144. The housing 140 includes heating device 146 having a fan or blower for forcing heated air though the housing 140 and onto the petri dishes. A suitable filter system can be included to maintain a sterile, dust free environment within the housing. An ultraviolet light source 148 is included within the housing. An ultraviolet light source 148 is included within the housing to emit germicidal UV rays to prevent contamination of the petri dish during the drying stage. The housing has a length sufficient to ensure the petri dishes exit the housing in a substantially dehydrated condition.

In the embodiment shown in FIG. 1, sterile air introduced by the sterilizing chamber 16 passes through the enclosure 21 of the dispensing and aspirating stations 18, 20 in a sweeping direction. The air continues to flow through the inlet opening 142 of dehydrating chamber 22 and eventually exits through outlet 144 of dehydrating chamber 22.

The amount of fluid material remaining in the petri dish after aspiration is determined by the amount of aspiration, the viscosity of the fluid material, the amount of gellable material in the fluid material, the gelling temperature of the fluid material, the temperature of the fluid, and the amount of gelling which has taken place. Generally, about 0.5 to 2.0 ml of the fluid material remains in the petri dish and preferably about 1.5 ml after aspiration. In embodiments, the fluid material is dispensed as a warm aqueous solution comprising 1–2% agar, low methoxyl pectin, or gellan gum. Alternatively, the fluid material is a plastic resin in a suitable solvent or carrier. The solution begins to solidify as soon as the solution contacts the cool surface of the petri dish.

Figure 8:
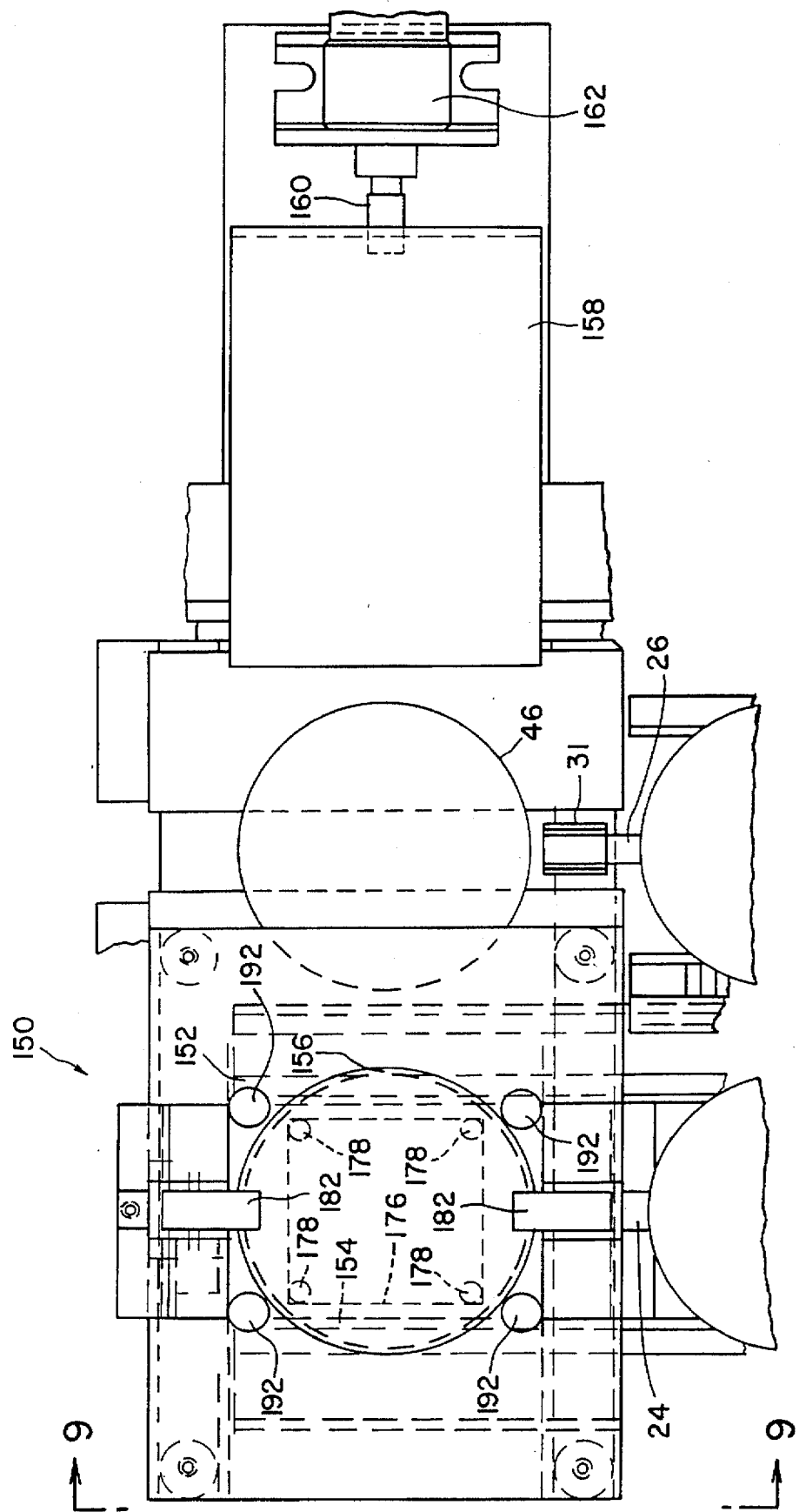
FIG. 8 is a partial top plan view of the restacking device showing the parallel conveyors, pusher plate and stacking assembly.
Figure 9:
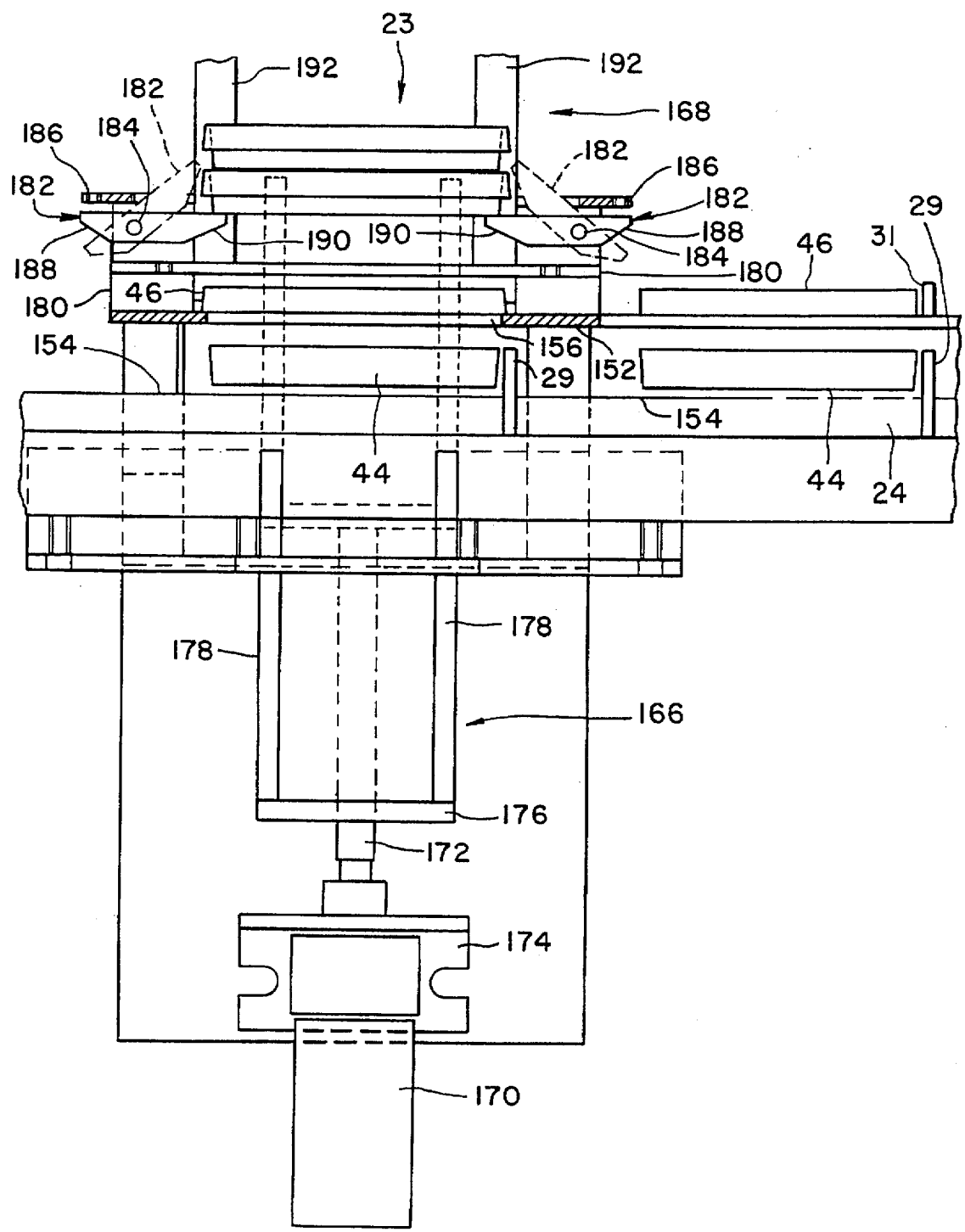
FIG. 9 is a partial side elevational view of the restacking device showing the lifting and stacking assembly.

After the fluid material in the petri dish is dehydrated, the petri dish exits the drying chamber and is advanced to the restacking assembly 150. Referring to FIGS. 8 and 9, restacking assembly 150 includes an upper plate 152 which is parallel to chain conveyor 26 and slide rails so that the lid 46 slides onto upper plate 152. Upper slide plate 152 is positioned above first chain conveyor 24 a distance sufficient to permit petri dish 44 to slide below upper plate 152. A lower slide plate 154 is positioned in the same plane as the first chain conveyor 24 to receive the petri dish 44 from the chain conveyor 24. Upper slide plate 152 includes an opening 156 above lower slide plate 154. The opening 156 is dimensioned to permit lid 46 to be positioned on the upper slide plate 152 over the opening 156 without falling through while being large enough to permit petri dish 44 to pass through.

A pusher plate 158 is positioned next to upper slide plate 152. Pusher plate 158 is coupled to rod 160 of pneumatic cylinder 162 which is actuated by microprocessor 11. Pneumatic cylinder 162 is actuated to extend rod 160 and pusher plate 158 away from cylinder 162 to engage the lid 46. Pusher plate 158 pushes lid 46 across upper plate 152 until lid 46 is substantially centered over opening 156 directly above petri dish 44. Pusher plate 158 then retracts to the starting position shown in FIG. 8.

A lifting device 166 is provided below lower slide plate 154 and the petri dish 44. A restacking rack 168 is provided immediately above lifting device 166. Lifting device 166 includes a pneumatic cylinder 170 coupled to a mounting plate 174 and cooperating piston rod 172 for vertical reciprocating movement. A substantially square horizontal plate 176 is coupled to the distal end of piston rod 172 and positioned parallel to the lower slide plate 154. Four rods 178 are coupled to the upper surface of plate 176 and extend upwardly perpendicular to the plate 176. In preferred embodiments, rods 178 are positioned in the corners of the plate 176 and are substantially uniformly spaced apart a distance to support the petri dish 44.

Piston rod 172 and plate 176 are normally in the retracted position shown in FIG. 9. Cylinder 170 is activated by microprocessor 11 to extend piston rod 172 and plate 176 upwardly so that rods 178 pass through the opening in lower plate 154 to engage the bottom of the petri dish as discussed hereinafter in greater detail.

Restacking rack 168 includes two support members 180 extending upwardly from upper slide plate 152 on opposite edges of the opening 156 as shown in FIG. 9. At the upper end of each support member 180 is a finger 182 pivotally connected thereto by a pivot pin 184. A finger stop member 186 is also coupled to the top of support member 180 to limit the pivotal movement of finger 182. As shown in FIG. 9, finger 182 is in a normal horizontal rest position with the trailing end 188 engaging finger stop member 186 and the leading end 190 extending inwardly toward opening 156. Finger 182 is pivotable from the horizontal position shown in FIG. 9 upwardly to the position shown in phantom lines. A plurality of support rods 192 extend upwardly from upper slide plate to receive a stack of the petri dishes. As shown in FIG. 8, four rods 192 are generally provided and spaced around the opening in upper slide plate 152 to permit stacking of the petri dishes 44.

In operation, the petri dish 44 and the associated lid 46 are advanced to the lower slide plate 154 and upper slide plate 152, respectively, by the parallel chain conveyors. Cylinder 162 is then actuated whereby push plate 158 pushes lid 46 across upper slide plate 152 and over opening 156. Push plate 158 is then retracted to the original position. Cylinder 170 is then actuated whereby lifting rods 178 move upwardly engaging the bottom of petri dish 44. Lifting rods 178 continue the upward movement, lifting petri dish 44 upward through opening 156 into the lid 46 to the reassembled position. Lifting rods 178 move upward further lifting the petri dish 44 and lid past fingers 182. Fingers 182 pivot upward to allow the petri dish 44 and lid 46 to pass, whereupon the fingers return to the original horizontal position. Lifting rods 178 are then retracted so that the petri dish and lid are retained in the restacking rack 168 by fingers 182. The cycle is then repeated with the petri dishes 44 and lids 46 being stacked between the rods 192.

As can be seen, the method and apparatus provide an efficient means for coating petri dishes or other containers with a coating material without the need to handle the dishes. The lids are separated from the dishes and filled in a sterile environment. The filled and dried containers are closed with the lids and stacked in the restacking assembly where they can be removed and packaged as needed. In the illustrated embodiment, the apparatus includes a single destacking unit with a pair of parallel chain conveyors for conveying the petri dish and lids. It will be understood that the apparatus can include more than one destacking unit, conveying system and restacking unit which can be operated by a single microprocessor control and power source.

The control unit shown in FIG. 1 is positioned on top of the drying chamber although in practice it can be located in any convenient location. The control unit preferably contains the necessary microprocessors to control and monitor the apparatus. The speed of the conveyor chains and stepwise advancement of the conveyor chains are coordinated with destacking, filling, aspiration and restacking steps so that the container is properly indexed to each station and advanced to the next station when the various dispensing, aspirating and drying cycles are completed.

While various advantageous embodiments have been selected to illustrate the invention, it will be understood by those skilled in the art that various changes and modifications can be made therein without departing from the scope of the invention as defined in the appended claims.

What is claimed is:

1. An apparatus for forming a layer of a fluid coating material in a container, said apparatus comprising:
   conveyor means for conveying the container through said apparatus;
   dispensing means for filling said container with an amount of the fluid coating material to cover the bottom of said container;
   first aspirating means for aspirating a portion of said coating material from said container and forming a uniform coating of said fluid coating material; and
   dehydrating means for dehydration of said coating material to form a substantially dehydrated, uniform coating of said coating material in said container.

2. The apparatus of claim 1, further comprising first tilting means for simultaneously tilting said container while being filled with said coating material, and for pooling an excess of said coating material along a first side of said container.

3. The apparatus according to claim 2, wherein said first tilting means is a pneumatically actuated plunger for engaging a bottom corner of said container and lifting said corner upwardly.

4. The apparatus according to claim 2, wherein said dispensing means is a dispensing nozzle disposed above said container for filling said container adjacent a second side of said container.

5. The apparatus according to claim 2, further comprising second tilting means downstream of said first tilting means, for tilting said container and pooling said coating material along a second side of said container, said first aspirating means being positioned for aspirating said pooled coating material along said second side.

6. The apparatus according to claim 5, wherein said second tilting means is a cam surface cooperating with said conveyor means for engaging a bottom face of said container and lifting a side edge of said bottom face with advancing movement of said container.

7. The apparatus according to claim 5, wherein said second tilting means tilts said container to pool said coating material to a second side opposite said first side.

8. The apparatus according to claim 7, further comprising a second aspirating means for removing said pooled coating material from said container, said second aspirating means being positioned downstream of said first aspirating means.

9. The apparatus according to claim 8, wherein said second tilting means is a cam surface cooperating with said second aspirating means for tilting said container to pool said coating material to said second side of said container, said second aspirating means being positioned above said second side for removing said pooled material.

10. The apparatus according to claim 5, further comprising
    third tilting means positioned downstream of said first aspirating means for tilting said container toward said first side after aspirating said material.

11. The apparatus according to claim 1, wherein said dehydrating means comprises a heated chamber for directing heated air onto said fluid coating material.

12. The apparatus according to claim 11, wherein said coating material includes a gel inducing agent and said dispensing means includes heating means for maintaining said coating material in a fluid condition.

13. The apparatus according to claim 12, wherein said dehydrating means comprises a heating element and a blower.

14. The apparatus according to claim 1, further comprising sterilizing means upstream of said dispensing means for directing sterile air onto said container.

15. The apparatus according to claim 14, wherein said sterilizing means comprises a chamber having an ultraviolet light source.

16. The apparatus according to claim 1, said conveyor means comprising first and second parallel conveyors operatively connected together, and motor means for advancing said conveyors in predetermined incremental steps.

17. The apparatus according to claim 16, further comprising
    a destacking device for receiving a plurality of said containers and a plurality of lids for said containers, said destacking device including means for separating said lids from said containers and positioning said containers on said first conveyor and said lid on said second conveyor.

18. The apparatus according to claim 17, wherein said destacking device comprises means for receiving a stack of said containers and lids assembled thereon,
    a horizontal plate having an opening therein dimensioned to allow said container to pass through said opening onto said first conveyor while supporting said lid, and
    slide means for sliding said lid from said horizontal plate onto said second conveyor.

19. The apparatus according to claim 18, said destacking device further comprising
    a vertically positioned pneumatic plunger movable from an upper position to receive said container to a lower position for lowering said container through said opening in said horizontal plate and onto said first conveyor.

20. The apparatus according to claim 16, further comprising
    a restacking assembly positioned at a downstream end of said conveyor means, said restacking assembly having a horizontal plate with an opening dimensioned to allow said container to pass through and to support said lid, a slide plate for sliding said lid onto said horizontal plate about said opening, and lifting means for lifting said container upward from said first conveyor through said opening in said horizontal plate to mate with said lid, and retaining means for retaining said lid and container in said restacking assembly.

21. A method of forming a coating on an inside bottom surface of a container, comprising the steps of:

filling said container with an amount of a liquid coating material in a dispensing station at an upstream end of a conveyor assembly, removing a portion of said coating material from said container and forming a coating of said material on said inside bottom surface, and drying said coating of said material in said container.

22. The method of claim 21, wherein said container is a petri dish and wherein said liquid coating material is a gellable material containing a gel inducing agent.

23. The method of claim 21, comprising filling said container at a first side of said container and simultaneously tilting said container toward a second side of said container.

24. The method of claim 21, further comprising tilting said container toward a first side subsequent to said filling step to pool said coating material at said first side while removing said portion of said material.

25. The method of claim 24, further comprising tilting said container toward said first side subsequent to said first removing step and removing pooled material from said container in a second removing step.

26. The method of claim 24, further comprising tilting said container toward a second side subsequent to said first removing step to uniformly distribute remaining coating material on said inside bottom surface.

27. The method of claim 21, wherein said removing step comprises aspirating said material from said container.

28. The method of claim 21, wherein said liquid coating material is a gellable solution, wherein said solution contains a gel inducing agent.

29. The method of claim 21, further comprising passing said container through a sterilizing chamber and subjecting said container to ultraviolet light.

30. The method of claim 21, wherein said drying step comprises subjecting said container to a flow of heated air.

31. The method of claim 30, said drying step further comprising subjecting said container to ultraviolet light to maintain sterility.

32. The method of claim 21, said filling step further comprising delivering said liquid coating material from a supply reservoir to said container, and said removing step comprises returning removed material from said container to said supply reservoir.

33. The method of claim 21, wherein said container includes a complementing lid and said method further comprises separating said lid from said container prior to filling said container, and replacing said lid on said container subsequent to said drying step.

34. The method of claim 33, comprising placing said container on a first conveyor and said lid on a second conveyor parallel to said first conveyor, and conveying said container through said filling station.

35. An apparatus for applying a substantially uniform layer of a coating material in a petri dish, said coating material comprising a gel inducing agent, said apparatus comprising:

filling means for filling a petri dish with a predetermined amount of the coating material;

first tilting means for tilting the petri dish for pooling the coating material to a side of the petri dish;

aspirating means for aspirating a portion of said pooled coating material from the petri dish and forming a uniform coating of said coating material; and dehydrating means for dehydrating said coating material remaining in the petri dish.

36. The apparatus of claim 35, further comprising tilting means for tilting the petri dish simultaneously with said filling means while filling said petri dish, and wherein said filling means dispenses said coating material adjacent a sidewall of the petri dish opposite the direction of tilt of the petri dish.

37. The apparatus of claim 35, further comprising tilting means for tilting the petri dish after said aspirating means removes said coating material to uniformly distribute said coating material.

38. A method of forming a substantially uniform coating on an inside bottom surface of a petri dish having a lid associated therewith comprising the steps of:

separating a petri dish from the lid and dispensing a predetermined amount of a solution containing a gel inducing agent, wherein said dispensing step dispenses an excess needed to cover the petri dish, aspirating said excess solution from the petri dish and forming a substantially uniform coating of the solution in the petri dish, drying said coating, and replacing the lid on the coated petri dish.

39. The method of claim 38, wherein said solution is a pectin-containing solution including a metal cation as a gel inducing agent, said method further comprising pouring a pectin-containing solution into said petri dish and gelling said pectin-containing solution.

40. The method of claim 38, comprising tilting the petri dish to pool the excess solution to a first side, and aspirating said pooled solution from the petri dish.

41. The method of claim 40, further comprising tilting the petri dish towards a second side opposite said first side to uniformly re-distribute the remaining solution in the petri dish.

* * * * *